United States Patent
Takaki et al.

(10) Patent No.: US 7,883,873 B2
(45) Date of Patent: *Feb. 8, 2011

(54) SACCHARIDE COMPOSITION SYNTHESIZER

(75) Inventors: Masanori Takaki, Hitachinaka (JP); Kuriko Yamada, Sapporo (JP); Kisaburo Deguchi, Sapporo (JP); Hiroaki Nakagawa, Sapporo (JP); Shinichiro Nishimura, Sapporo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 865 days.

This patent is subject to a terminal disclaimer.

(21) Appl. No.: 11/060,810

(22) Filed: Feb. 18, 2005

(65) Prior Publication Data

US 2005/0221472 A1 Oct. 6, 2005

(30) Foreign Application Priority Data

Mar. 31, 2004 (JP) .............................. 2004-105562

(51) Int. Cl.
*C12P 19/18* (2006.01)
*C12P 19/16* (2006.01)
*B01J 19/00* (2006.01)

(52) U.S. Cl. ............................ 435/97; 435/72; 435/100; 435/101; 435/137; 435/289.1; 422/131; 422/132; 422/134; 422/234; 422/69; 422/70; 536/18.5; 536/124; 127/34; 127/42

(58) Field of Classification Search ................... 435/97, 435/72, 100, 101, 137, 289.1; 422/131, 132, 422/234, 69, 70; 536/18.5, 124; 127/34, 127/42

See application file for complete search history.

(56) References Cited

U.S. PATENT DOCUMENTS

| 5,288,637 | A | 2/1994 | Roth et al. |
| 5,651,943 | A | 7/1997 | Lam et al. |
| 6,046,040 | A | 4/2000 | Nishiguchi et al. |
| 6,423,833 | B1* | 7/2002 | Catani et al. ................ 536/18.5 |
| 2002/0061550 | A1* | 5/2002 | Roth .......................... 435/68.1 |
| 2002/0085964 | A1* | 7/2002 | Seeberger et al. ........... 422/190 |

FOREIGN PATENT DOCUMENTS

EP      1352967 A     10/2003

(Continued)

OTHER PUBLICATIONS

European Search Report dated Feb. 6, 2007.

*Primary Examiner*—Nathan A Bowers
(74) *Attorney, Agent, or Firm*—Dickstein Shapiro LLP

(57) ABSTRACT

The present invention provides a sugar chain synthesizer capable of continuously reacting sugar chains when a plurality of sugar chains are successively reacted. The sugar chain synthesizer of the present invention includes a plurality of vessels containing respective sugar nucleotide solutions, a plurality of vessels containing respective glycosyltransferases, and a reactor containing a primer that is a water-soluble polymer, into which the above described sugar nucleotide solution and glycosyltransferase are introduced. In the present invention, components in a reaction solution obtained in the reactor are separated through an ultrafiltration column, and a reaction product is then returned to the above described reactor, so as to continuously synthesize sugar chains. Although it is a complicated synthesis of sugar chains, it becomes possible to carry out such synthesis continuously and automatically.

9 Claims, 3 Drawing Sheets

FOREIGN PATENT DOCUMENTS

| | | |
|---|---|---|
| EP | 1405905 A | 4/2004 |
| JP | 60054398 | 3/1985 |
| JP | 5-500905 | 2/1993 |
| JP | 11-42096 | 2/1999 |
| WO | WO 03/004597 A | 1/2003 |

* cited by examiner

US 7,883,873 B2

SACCHARIDE COMPOSITION SYNTHESIZER

INCORPORATION BY REFERENCE

The present application claims priority from Japanese application JP2004-105562 filed on Mar. 31, 2004, the content of which is hereby incorporated by reference into this application.

BACKGROUND OF THE INVENTION

The present invention relates to a technique of synthesizing and separating a sugar chain. In particular, the present invention relates to a sugar chain synthesizer used to automatically perform such processes.

Complex carbohydrates play important roles in cells, such as information transmission, or intracellular differentiation such as recognition of viruses, cancer cells, or blood types. Clarification of the functions of sugar chains is considered to be a post-genome project. Methods for synthesizing oligonucleic acids or peptides have already been provided and automated. However, a method for synthesizing a sugar chain still has many problems.

In order to clarify the functions of sugar chains, the establishment of a method for synthesizing a sugar chain and realization of an efficient synthesizer have been desired. At present, the following three methods for synthesizing a sugar chain have been applied:

(1) a method of using chemical synthesis;
(2) a fermentation method of using genetically-altered cells or microorganisms; and
(3) a synthetic method of using glycosyltransferase.

The method in (1) above is complicated and has many reaction steps because sugar chains of interest are successively synthesized while protecting OH groups other than the OH group to be chemically bound. The method in (2) above enables the mass production of sugar chains of interest, but the following purification process becomes complicated. The method in (3) above has been developed to overcome the complexity of the methods in (1) and (2) above, and it is disclosed in JP-A-11-42096 (Patent Document 1) for example. In addition, since the method in (3) above involves a selective synthesis using glycosyltransferase, differing from the method in (1) above, it is not necessary to protect OH groups. Moreover, since this method causes only small quantities of by-products, the purification process following the synthesis is easy.

A sugar chain synthesizer is disclosed in JP-A-5-500905 (Patent Document 2).

When the synthesis of sugar chains is carried out by the method described in (3) above actually using a synthesizer, a batch system is currently applied to successively react a plurality of sugars. In the batch system, separation and purification of a product is carried out in every step, and then, the routine goes to the next reaction. In order to carry out all processes, human power is absolutely necessary.

In the case of the synthesizer disclosed in the aforementioned Patent Document 2, it is necessary to continuously connect reaction columns with separation and purification means in series, depending on the order of sugars to be reacted. That is to say, this synthesizer is problematic in that although the sugars to be reacted are of the same type, reaction columns and separation and purification means are required depending on the number of the sugars to be reacted, and in that the synthesizer should be large-scale equipment.

In addition, Patent Document 2 does not describe a method for automatically and continuously synthesizing sugar chains.

It is an object of the present invention to provide a sugar chain synthesizer, in which when a plurality of sugars are successively reacted, a single reactor and one or more separation means are used, and reaction products or glycosyltransferases are recovered and recycled, so as to continuously carry out every reaction steps.

In order to achieve the aforementioned object, the sugar chain synthesizer of the present invention is characterized in that it comprises: a pump for supplying a buffer solution; a plurality of vessels containing respective sugar nucleotide solutions; a plurality of vessels containing respective glycosyltransferases; a reactor containing a primer that is a water-soluble polymer, into which the above described sugar nucleotide solutions and glycosyltransferases are introduced; a sampling means for sampling the solution contained in the above described reactor and introducing it into a flow channel through which the above described buffer solution flows; a first ultrafilter for subjecting the solution introduced by the above described sampling means to ultrafiltration; a second ultrafilter for subjecting an effluent from the above described first ultrafilter to ultrafiltration; a first selector valve, which is provided between the above described first and second ultrafilters and comprises a flow channel for returning the effluent from the above described first ultrafilter to the above described reactor and a flow channel for supplying the effluent to the above described second ultrafilter; and a second selector valve, which is provided downstream of the above described second ultrafilter and comprises a flow channel for delivering the effluent from the above described second ultrafilter to a drain and a flow channel for supplying the effluent to the above described vessel containing respective glycosyltransferase.

In addition, the sugar chain synthesizer of the present invention is further characterized in that it comprises: a pump for supplying a buffer solution; a plurality of vessels containing respective sugar nucleotide solutions; a plurality of vessels containing respective glycosyltransferases; a reactor containing a primer that is a water-soluble polymer, into which the above described sugar nucleotide solutions and glycosyltransferases are introduced; a sampling means for sampling the solution contained in the above described reactor and introducing it into a flow channel through which the above described buffer solution flows; a GPC column for separating the solution introduced by the above described sampling means depending on the molecular weight; first and second ultrafilters, into which an eluant from the above described GPC column is introduced; a first selector valve, which is provided between the above described GPC column and the above described first and second ultrafilters, and selectively supplies the eluant from the above described GPC column to the above described first ultrafilter or the above described second ultrafilter; a second selector valve, which is provided downstream of the above described first ultrafilter and comprises a flow channel for supplying an effluent from the above described first ultrafilter to the above described reactor and a flow channel for delivering the effluent to a drain; and a third selector valve, which is provided downstream of the above described second ultrafilter and comprises a flow channel for delivering the effluent from the above described first ultrafilter to the above described drain and a flow channel for supplying the effluent to the above described vessel containing respective glycosyltransferase.

According to the present invention, it becomes possible to return an effluent (reaction product) that had once passed through a reactor and a separation column to the reactor and the separation column again. By repeating such a process, it becomes possible to continuously and automatically carry out a complicated synthesis of sugar chains.

Other objects, features and advantages of the invention will become apparent from the following description of the embodiments of the invention taken in conjunction with the accompanying drawings.

EXPLANATION OF NUMERICAL SYMBOLS

1 ... buffer solution; 2 ... pump; 3 autosampler; 4 ... water-soluble primer; 5 reactor; 6, 6' ... ultrafilters; 7,7' ... hexagonal valves; 8 ... flow channel selector valve; 9 ... controller; 10 to 13 ... sugar nucleotide solutions ($S_1, S_2, S_3$); 14 to 17 ... glycosyltransferases ($E_1, E_2, E_3$); 18 and 19 detectors; 22 ... GPC column

PREFERRED EMBODIMENTS OF THE INVENTION

EXAMPLE 1

Figure 1:
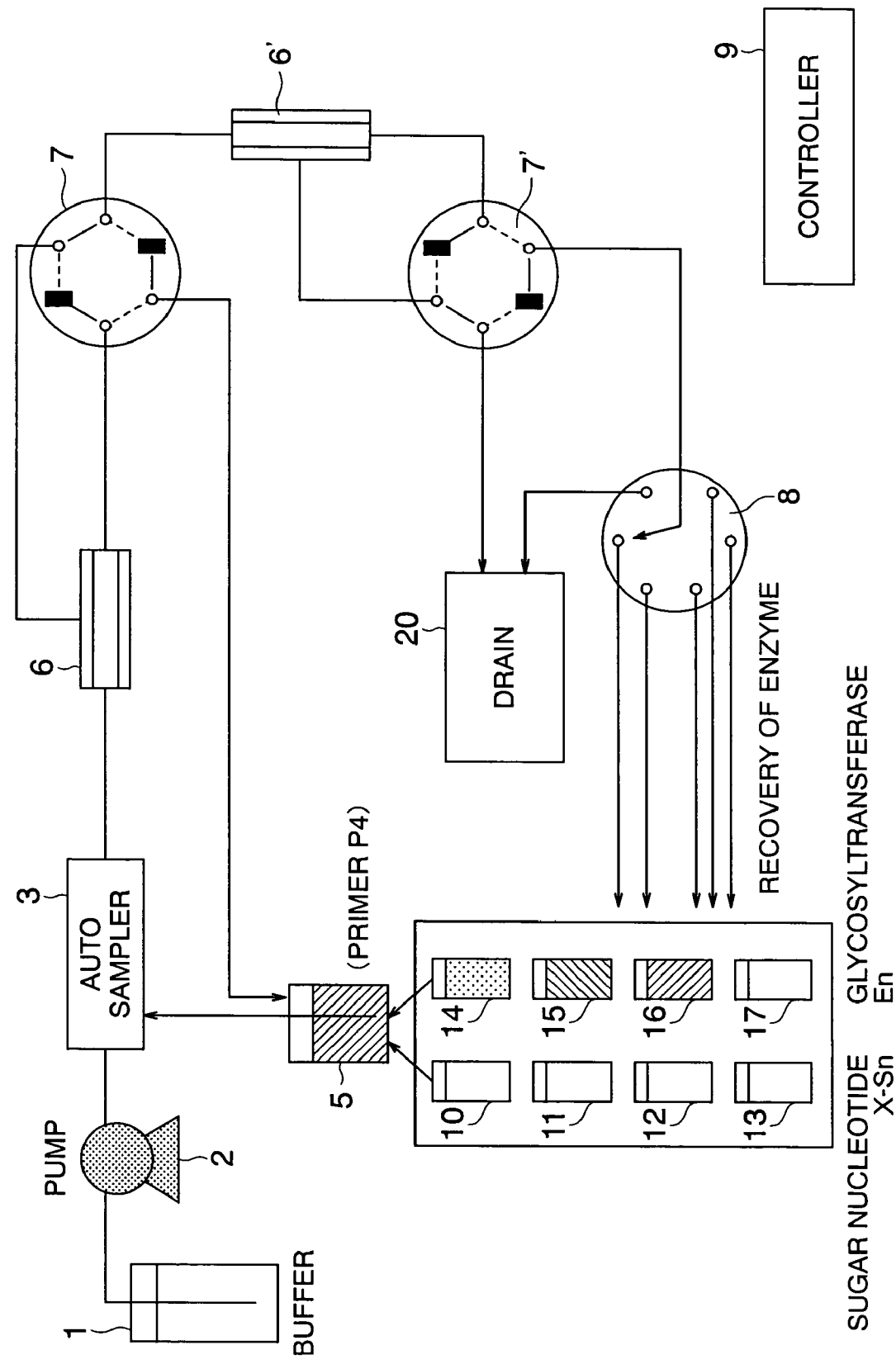
FIG. 1 shows the system configuration and flow channels of a sugar chain synthesizer in Example 1.

FIG. 1 shows the system configuration of flow channels in the present embodiment.

The sugar chain synthesizer is composed of: a pump 2 for supplying a buffer solution 1; a plurality of storage vessels containing various types of sugar nucleotide solutions 10 to 13; a plurality of storage vessels containing various types of glycosyltransferases 14 to 17; an autosampler 3 equipped with a single reactor 5; an ultrafilter (1) 6 for separating an effluent from the autosampler 3; a hexagonal valve 7 for introducing an effluent from the ultrafilter (1) 6 into the reactor 5 or an ultrafilter (2) 6'; another ultrafilter (2) 6' for filtrating glycosyltransferase from the mixture of glycosyltransferase, sugar nucleotide, and nucleotide eluted from the ultrafilter (1) 6; a hexagonal valve 7' for introducing an effluent from the ultrafilter (2) 6' into a drain 20 or a flow channel selector valve 8; the flow channel selector valve 8 for introducing the glycosyltransferase after filtration into any one of the original storage vessels or the drain 20; and a controller 9 for controlling these units.

A primer 4 has previously been stored in the reactor 5. The above autosampler 3 initiates a catalytic reaction, when any one of the sugar nucleotide solutions 10 to 13 and any one of the glycosyltransferases 14 to 17 are added to the reactor 5, and then, it samples a solution obtained as a result of the reaction and supplies it to a flow channel. All of the reactor 5, the sugar nucleotide solutions 10 to 13, and the glycosyltransferases 14 to 17 are adjusted at their optimal temperatures and maintained.

In addition, in the hexagonal valves 7 and 7', the round portions indicate ports connecting with external flow channels, and the filled square portions indicate ports that are blocked against flow channels. The solid-line flow channels and the broken-lines flow channels can alternatively be changed to one another.

Moreover, hydrolase can be used instead of the aforementioned glycosyltransferase.

Examples of the glycosyltransferases 14 to 17 used in the present synthesizer may include galactose transferase, N-acetylglucosamine transferase, N-acetylgalactosamine transferase, fucose transferase, sialic acid transferase, and mannose transferase. The term a "reaction product" is used herein to mean a product formed by binding one or more monosaccharides or sugar chains to the primer 4 that is a water-soluble polymer (a water-soluble polymer having a molecular weight distribution), or a product formed by binding one or more monosaccharides or sugar chains to a monodisperse dendrimer. Examples of such a reaction product may include biopolymers such as a protein, glycoprotein, glycopeptide, lipid, glycolipid, oligosaccharide, or polysaccharide, synthetic polymers such as a polyacrylamide derivative described in the aforementioned Patent Document 1, and dendrimers. Those having a molecular weight of 5,000 or greater are more preferable. In the present embodiment, such a reaction product means a product (hereinafter referred to as a primer (P-Sn)) formed by chemically binding a primer (hereinafter referred to as P) with a sugar (Sn). Examples of the sugar nucleotide solutions 10 to 13 may include uridine-5'-diphosphogalactose, uridine-5'-diphos-N-acetylglucosamine, uridine-5'-diphos-N-acetylgalactosamine, guanosine-5'-diphosphofucose, guanosine-5'-diphosphomannose, and cytidine-5'-monophospho-N-acetylneuraminic acid. In the present embodiment, such a sugar nucleotide solution is hereinafter referred to as Xn-Sn.

The operation of the present synthesizer will be described below based on FIG. 1.

In FIG. 1, the sugar nucleotide 10 contains ($X_1$-$S_1$), the sugar nucleotide 11 contains ($X_2$-$S_2$), and the sugar nucleotide 13 contains ($X_3$-$S_3$).

Herein, it is assumed that the primer P and the sugars $S_1, S_2$, and $S_3$ are reacted in the order of P-$S_1$-$S_2$-$S_3$. However, in reality, the order of the sugars $S_1, S_2$, and $S_3$ is not limited, and $S_1$ can also be repeated such that the order becomes P-$S_1$-$S_2$-$S_1$-$S_3$.

When the reaction is carried out in the order of P-$S_1$-$S_2$-$S_3$, the present synthesizer basically includes the following 3 steps:

Step 1 (mixing of samples): A certain amount of the sugar nucleotide 10 ($X_1$-$S_1$) is measured and sampled with the autosampler 3, and it is then introduced into the reactor 5. Subsequently, the glycosyltransferase 14 was also introduced into the reactor 5. Thereafter, these components were reacted with the primer (P) 4 at a certain temperature for a certain period of time by stirring with a stirring bar or magnet stirrer. During this step, it is also possible to stir the mixture by repeatedly aspirating and discharging the solution contained in the reactor 5 with a nozzle for the aforementioned measuring sampling.

Step 2 (ultrafiltration): After completion of the reaction, the total solution contained in the reactor is sampled with the autosampler 3, and it is introduced into a flow channel system and then introduced into the ultrafilter (1) 6. The solution contains the reaction product primer (P-$S_1$), the glycosyltransferase 14, an unreacted sugar nucleotide ($X_1$-$S_1$), and a nucleotide ($X_1$) as a reaction by-product.

Herein, the flow rate of the pump 2 is increased, so as to filtrate (separate) the reaction product primer (P-$S_1$) from other components (the glycosyltransferase, the unreacted sugar nucleotide ($X_1$-$S_1$), and the nucleotide ($X_1$) as a reaction by-product) The reaction product primer (P-$S_1$) is eluted from the bottom of the ultrafilter (1) 6, and other components are eluted from the lateral portion of the ultrafilter (1) 6.

A filter that separates only the reaction product primer that is a water-soluble polymer but filtrates other components including glycosyltransferase is selected as a filter used in the ultrafilter (1) 6. That is to say, the water-soluble polymer used herein needs to have a molecular weight that is 2 times or more the molecular weight of glycosyltransferase.

The hexagonal valves 7 and 7' have flow channels indicated with the solid lines. The glycosyltransferase, the unreacted sugar nucleotide ($X_1$-$S_1$), and the nucleotide ($X_1$) as a reaction by-product that are eluted from the ultrafilter (1) 6 are introduced into another ultrafilter (2) 6' via the flow channels of the hexagonal valve 7 indicated with the solid lines. The reaction product primer (P-$S_1$) remains at the position of the hexagonal valve 7.

In the ultrafilter (2) 6', the glycosyltransferase is filtrated (separated) from other components (the unreacted sugar nucleotide ($X_1$-$S_1$) and the nucleotide ($X_1$) as a reaction by-product. The unreacted sugar nucleotide ($X_1$-$S_1$) and the nucleotide ($X_1$) as a reaction by-product are eluted from the lateral portion of the ultrafilter (2) 6', and these components are then discharged to the drain 20 via the flow channels of the hexagonal valve 7' indicated with the solid lines. The glycosyltransferase 14 remains at the position of the hexagonal valve 7' located at the bottom of the ultrafilter (2) 6'. A filter, which can filtrate and separate glycosyltransferase that is a polymeric protein from low molecular weight compounds, the unreacted sugar nucleotide ($X_1$-$S_1$) and the nucleotide ($X_1$) as a reaction by-product, is selected as a filter used in the ultrafilter (2) 6'.

Step 3 (Recovery): After completion of sufficient filtration, the flow channels indicated with the solid lines are switched to the flow channels indicated with the broken lines in the hexagonal valve 7, so as to recover the reaction product primer (P-$S_1$) to the reactor 5. Thereafter, the flow channels are again switched to the original flow channels in the hexagonal valve 7. Subsequently, the flow channels indicated with the solid lines are switched to the flow channels indicated with the broken lines in the hexagonal valve 7', and the flow channel selector valve 8 is actuated, so as to recover glycosyltransferase to the original storage vessel. Thereafter, in the hexagonal valves 7 and 7', the flow channels are again switched to the original flow channels, and the flow rate of the pump 2 is decreased.

The aforementioned steps 1 to 3 are successively repeatedly carried out on a sugar nucleotide ($X_2$-$S_2$) and a sugar nucleotide ($X_3$-$S_3$), so that a reaction product primer (P-$S_1$-$S_2$-$S_3$) can be obtained in the reactor 5. Then, the reaction product primer (P-$S_1$-$S_2$-$S_3$) is captured from the reactor 5, so as to obtain a final reaction product primer.

The procedures for synthesizing a sugar chain (P-$S_1$-$S_2$-$S_3$) in the present embodiment are as described above.

If a dendrimer having a molecular weight smaller than that of glycosyltransferase is used as a primer P (4), in the solution contained in the reactor 5 obtained after the reaction by the aforementioned step 1, are present the glycosyltransferase 14, the reaction product primer (P-$S_1$), the unreacted sugar nucleotide ($X_1$-$S_1$), and the nucleotide ($X_1$) as a reaction by-product, in the order of decreasing the molecular weight. Thus, since it becomes impossible to filtrate only the reaction product primer (P-$S_1$) to return to the reactor 5, such a dendrimer cannot be used as a primer P (4) in the present embodiment.

In addition, if glycosyltransferase is not recovered, the ultrafilter (2) 6', the hexagonal valve 7', and the flow channel selector valve 8 are not necessary, and the operations in which these units are used are also not necessary in the aforementioned steps.

EXAMPLE 2

Figure 2:
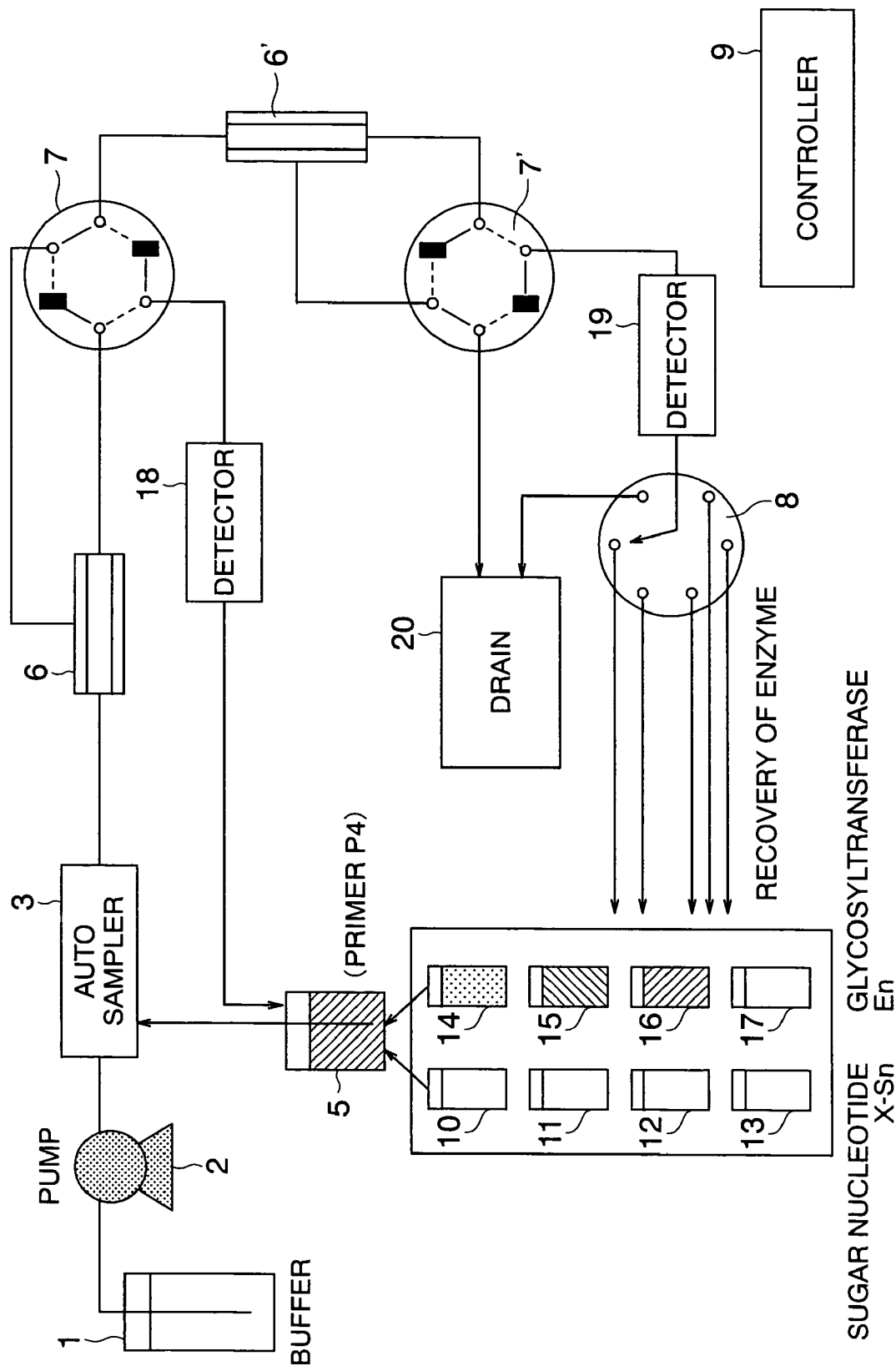
FIG. 2 shows the system configuration and flow channels of a sugar chain synthesizer in Example 2.

FIG. 2 shows a modified embodiment of Example 1. The figure shows the case where a detector (1) 18 and a detector (2) 19 are added. Any one selected from the group consisting of a refractive index detector (RI), an ultraviolet-visible detector (UV), and a diode array detector (DAD) can be used as each of the above detectors.

When the filtrated reaction product primer or glycosyltransferase is recovered, the detector (1) 18 and the detector (2) 19 are used to monitor whether or not the recovery is normally carried out, or to calculate the recovery rate. These detectors are useful in that in case that the recovery is not normally carried out for a certain reason, the subsequent synthetic reaction is suspended, and the waste of sugar nucleotides, glycosyltransferases, and time can be prevented.

EXAMPLE 3

Figure 3:
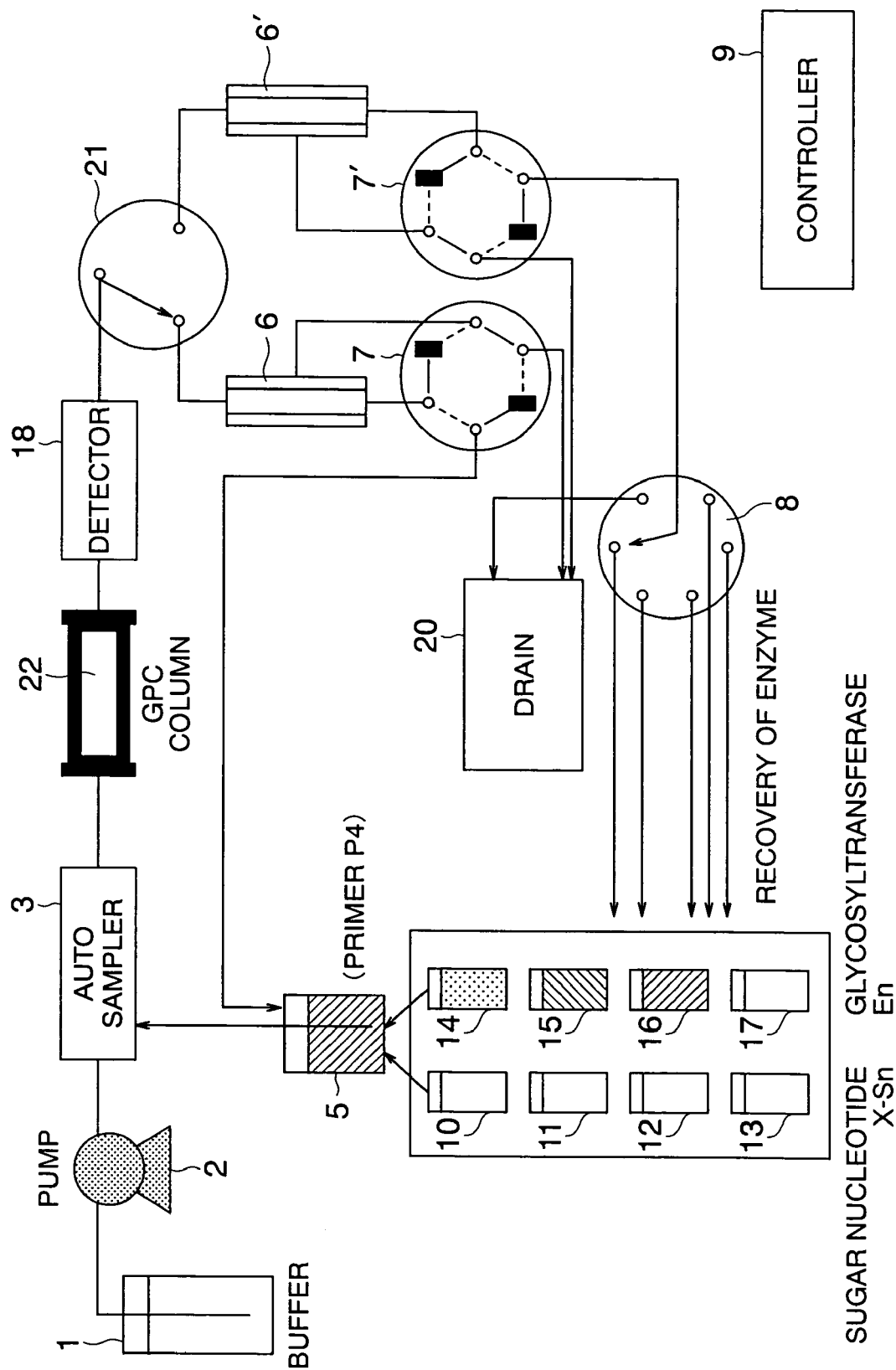
FIG. 3 shows the system configuration and flow channels of a sugar chain synthesizer in Example 3.

FIG. 3 shows the configuration of a synthesizer and flow channels in another embodiment. The components identical to those in Example 1 have the same numerical symbols as those in Example 1. As with Example 1, a filter that separates only a reaction product primer (P-$S_1$) that is a water-soluble polymer but filtrates other components is selected as a filter used in an ultrafilter (1) 6 in the present embodiment. As with Example 1, a filter that separates only glycosyltransferase but filtrates other components is selected as a filter used in an ultrafilter (2) 6'.

The operation of the present apparatus will be described below based on FIG. 3.

As with the aforementioned Example 1, when the reaction is carried out in the order of P-$S_1$-$S_2$-$S_3$, the present synthesizer basically includes the 4 steps described below.

The steps applied are different depending on whether the molecular weight of a component used as a primer (P) 4 is larger or smaller than that of glycosyltransferase. A dendrimer is an example of the component used as a primer (P) 4 having a molecular weight smaller than that of glycosyltransferase. Other components generally have a molecular weight larger than that of glycosyltransferase.

Thus, the case of using a primer (P) 4 having a molecular weight larger than that of glycosyltransferase will be first described.

Step 1 (mixing of samples): A certain amount of a sugar nucleotide ($X_1$-$S_1$) 10 is measured and sampled with an autosampler 3, and it is then introduced into a reactor 5. Subsequently, a glycosyltransferase 14 was also introduced into the reactor 5. Thereafter, these components were reacted with a primer (P) 4 at a certain temperature for a certain period of time by stirring with a stirring bar or magnet stirrer. During this step, it is also possible to stir the mixture by repeatedly aspirating and discharging the solution contained in the reactor 5 with a nozzle for the aforementioned measuring sampling.

Step 2 (Separation with GPC column): After completion of the reaction, the total solution contained in the reactor 5 is sampled and then introduced into a flow channel system. The flow rate of a pump is increased, and the solution is introduced into a GPC column 22. The solution contains the reaction product primer (P-$S_1$), the glycosyltransferase, an unreacted sugar nucleotide ($X_1$-$S_1$), and a nucleotide ($X_1$) as a reaction by-product. GPC column is an abbreviated name of a high performance gel permeation chromatography column, and the inside of the GPC column is filled with a filler. When a sample is introduced therein, if the sample consists of molecules small enough to permeate into the filler, it remains in the filler for a long period of time, and thus, an elution time is prolonged. In contrast, if the sample consists of large molecules, it does not remain in the filler but just passes through it, an elution time is shortened. That is to say, this GPC column successively elutes and separates samples in the order of decreasing the molecular weight. Accordingly, as a GPC column 22 used herein, a column that can sufficiently separate the reaction product primer (P-$S_1$), the glycosyltransferase, and the unreacted sugar nucleotide ($X_1$-$S_1$), depending on the difference of their molecular weights, is selected.

The components are eluted from the GPC column 22 in the order of decreasing the molecular weight. That is, the components are eluted in the order of the reaction product primer (P-$S_1$), the glycosyltransferase, the unreacted sugar nucleotide ($X_1$-$S_1$), and the nucleotide ($X_1$) as a reaction by-product. Such elution is monitored with a detector 18.

Step 3 (Ultrafiltration): At this point, a flow channel selector valve 21 is connected with the side of the ultrafilter (1) 6. Moreover, hexagonal valves 7 and 7' have flow channel indicated with the solid lines.

While it is confirmed with the detector 18 that the reaction product primer (P-$S_1$) is eluted, the flow channel selector valve 21 is connected with the side of the ultrafilter (1) 6 and continuously introduces the obtained effluent into the ultrafilter (1) 6. Since the flow channels of the hexagonal valve 7 are those indicated with the solid lines at the time, the reaction product primer (P-$S_1$) is blocked. However, other components are filtrated and delivered to a drain 20.

As with Example 2, any one selected from the group consisting of a refractive index detector (RI), an ultraviolet-visible detector (UV), and a diode array detector (DAD) can be used as such a detector 18.

When it is confirmed with the detector 18 that the glycosyltransferase is eluted instead of the reaction product primer (P-$S_1$), the flow channel selector valve 21 is switched, so that the glycosyltransferase is introduced into an ultrafilter (2) 6'. Since the flow channels of the hexagonal valve 7' are those indicated with the solid lines at the time, the glycosyltransferase is blocked. However, other components are filtrated and supplied to the drain 20.

Although it can be confirmed with the detector 18 that the elution of the glycosyltransferase was terminated, the solution (buffer) is continuously flown until the unreacted sugar nucleotide ($X_1$-$S_1$) and the nucleotide ($X_1$) as a reaction by-product are all discharged to the drain 20. By this operation, the glycosyltransferase and other components can sufficiently be filtrated with the ultrafilter (2) 6'.

Thereafter, the flow channel selector valve 21 is returned to the side of the ultrafilter (1) 6. The buffer is flown, and the reaction product primer (P-$S_1$) is filtrated again.

Since the reaction product primer (P-$S_1$) and the glycosyltransferase are eluted from the bottoms of the ultrafilters (1) 6 and (2) 6', the flow channels are blocked. The unreacted sugar nucleotide ($X_1$-$S_1$) and the nucleotide ($X_1$) as a reaction by-product that have been eluted from the lateral portions of the ultrafilters (1) 6 and (2) 6' are flown to the drain 20.

Step 4 (Recovery): After the reaction product primer (P-$S_1$) has sufficiently been filtrated, the hexagonal valve 7 is switched, so as to recover the reaction product primer (P-$S_1$) 4 to the reactor 5. Thereafter, the flow channel selector valve 21 is again switched to the side of the ultrafilter (2) 6', and further, the hexagonal valve 7' and the flow channel selector valve 8 are switched, so as to recover the glycosyltransferase to the original storage vessel. Thereafter, the flow channel valve 21 and the hexagonal valves 7 and 7' are returned to the original positions, and the flow rate of the pump 2 is decreased.

The aforementioned steps 1 to 4 are successively repeatedly carried out on a sugar nucleotide ($X_2$-$S_2$) and a sugar nucleotide ($X_3$-$S_3$), so as to obtain a final reaction product primer (P-$S_1$-$S_2$-$S_3$) in the reactor 5.

Next, the case of using a primer (P) 4 (dendrimer) having a molecular weight smaller than that of glycosyltransferase will be described.

When a dendrimer is used, the order in which components are eluted from a GPC column 22 is glycosyltransferase, a reaction production primer (P-$S_1$), an unreacted sugar nucleotide ($X_1$-$S_1$), and a nucleotide ($X_1$) as a reaction by-product. Thus, step 3 in this case differs from step 3 in the above embodiment. Step 3 in this case will be described below. It is to be noted that steps 1, 2, and 4 are the same as those in the above embodiment, the descriptions of these steps are omitted.

Step 3 (Ultrafiltration): When an eluant from the GPC column 22 is detected with a detector 18, a flow channel selector valve 21 is connected with the side of an ultrafilter (2) 6'. Hexagonal valves 7 and 7' are those indicated with the solid lines.

While it is confirmed with the detector 18 that the glycosyltransferase is eluted, the flow channel selector valve 21 is connected with the side of the ultrafilter (2) 6' and continuously introduces the obtained effluent into the ultrafilter (2) 6'. Since the flow channels of the hexagonal valve 7' are those indicated with the solid lines at the time, the glycosyltransferase is blocked. However, other components are filtrated and supplied to a drain 20.

When it is confirmed with the detector 18 that the reaction product primer (P-$S_1$) is eluted instead of the glycosyltransferase, the flow channel selector valve 21 is switched, so that the reaction product primer (P-$S_1$) is introduced into an ultrafilter (1) 6. Since the flow channels of the hexagonal valve 7 are those indicated with the solid lines at the time, the reaction product primer (P-$S_1$) is blocked. However, other components are filtrated and supplied to the drain 20.

Although it can be confirmed with the detector 18 that the elution of the reaction product primer (P-$S_1$) was terminated, the solution (buffer) is continuously flown until the unreacted sugar nucleotide ($X_1$-$S_1$), and the nucleotide ($X_1$) as a reaction by-product are all discharged to the drain 20. By this operation, the reaction product primer (P-$S_1$) and other components can sufficiently be filtrated with the ultrafilter (1) 6.

Thereafter, the flow channel selector valve 21 is returned to the side of the ultrafilter (2) 6'. The buffer is flown, and the glycosyltransferase is filtrated again.

Step 3 in the case of using a primer (P) 4 (dendrimer) having a molecular weight smaller than that of glycosyltransferase is as described above.

The procedures for synthesizing a sugar chain (P-$S_1$-$S_2$-$S_3$) in the present embodiment are as described above. In the present embodiment, since the synthesizer comprises the GPC column 22 and two ultrafilters are connected with each other in parallel, a primer (P) 4 having a molecular weight smaller than that of glycosyltransferase can be used, which cannot be used in Examples 1 and 2.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A sugar chain synthesizer, which comprises:
   a pump for supplying a buffer solution;
   a plurality of vessels containing a respective plurality of sugar nucleotide solutions;
   a plurality of vessels containing a respective plurality of glycosyltransferases corresponding to the plurality of sugar nucleotide solutions, wherein said glycosyltransferases are not immobilized;
   a single reactor containing a primer that is a water-soluble polymer, for successively introducing said plurality of corresponding sugar nucleotide solutions and glycosyltransferases;
   a sampling means for sampling a solution contained in said reactor and introducing it into a flow channel through which said buffer solution flows;
   a first ultrafilter for subjecting the solution introduced by said sampling means to ultrafiltration;
   a second ultrafilter for subjecting a first effluent from said first ultrafilter to ultrafiltration;
   a first selector valve, which is provided between said first and second ultrafilters and comprises a flow channel for returning a second effluent from said first ultrafilter to said reactor and a flow channel for supplying the first effluent from said first ultrafilter to said second ultrafilter; and
   a second selector valve, which is provided downstream of said second ultrafilter and comprises a flow channel for delivering a first effluent from said second ultrafilter to a drain and a flow channel for supplying a second effluent from said second ultrafilter to one of said vessels containing respective glycosyltransferases,
   wherein the operation from introducing the respective sugar nucleotide solutions into the reactor to delivering the second effluent from said second ultrafilter to the vessel containing the glycosyltransferase is repeatedly carried out for successive ones of said corresponding plurality of sugar nucleotide solutions and glycosyltransferases within the single reactor.

2. The sugar chain synthesizer according to claim 1, wherein the solution sampled from said reactor comprises a reaction product primer, a glycosyltransferase, an unreacted sugar nucleotide, and a nucleotide by-product, and wherein, in said first ultrafilter, the reaction product primer is separated from other components.

3. The sugar chain synthesizer according to claim 2, wherein the solution introduced into said second ultrafilter comprises the glycosyltransferase, the unreacted sugar nucleotide, and the nucleotide by-product, and wherein, in said second ultrafiltration column, the glycosyltransferase is separated from other components.

4. The sugar chain synthesizer according to claim 1, wherein a third switching flow channel for returning the second effluent from said second ultrafilter to any one of the vessels containing respective glycosyltransferases is provided in a flow channel between said second selector valve and said vessels containing respective glycosyltransferases.

5. The sugar chain synthesizer according to claim 1, wherein a first detector is provided in a flow channel between said first selector valve and said reactor, and a second detector is provided in a flow channel between said second selector valve and said vessels containing respective glycosyltransferases.

6. The sugar chain synthesizer according to claim 5, wherein each of said first and second detectors is any one selected from the group consisting of a refractive index detector (RI), an ultraviolet-visible detector (UV), and a diode array detector (DAD).

7. A sugar chain synthesizer, which comprises:
   a pump for supplying a buffer solution;
   a plurality of vessels containing respective sugar nucleotide solutions;
   a plurality of vessels containing respective glycosyltransferases, wherein said glycosyltransferases are not immobilized;
   a reactor containing a primer that is a water-soluble polymer, for introducing said sugar nucleotide solutions and glycosyltransferases;
   a sampling means for sampling the solution contained in said reactor and introducing it into a flow channel through which said buffer solution flows;
   a GPC column for separating the components in the solution introduced by said sampling means depending on the molecular weights thereof;
   first and second ultrafilters, into which an eluant from said GPC column is introduced;
   a first selector valve, which is provided between said GPC column and said first and second ultrafilters, and selectively supplies the eluant from said GPC column to said first ultrafilter or said second ultrafilter;
   a second selector valve, which is provided downstream of said first ultrafilter and comprises a flow channel for supplying a first effluent from said first ultrafilter to said reactor and a flow channel for delivering a second effluent from said first ultrafilter to a drain; and
   a third selector valve, which is provided downstream of said second ultrafilter and comprises a flow channel for delivering a first effluent from said second ultrafilter to said drain and a flow channel for delivering a second effluent from said second ultrafilter to one of said vessels containing respective glycosyltransferase,
   wherein the operation from introducing the respective sugar nucleotide solutions into the reactor to delivering the second effluent from said second ultrafilter to the vessel containing the glycosyltransferase is repeatedly carried out.

8. The sugar chain synthesizer according to claim 7, wherein a third switching flow channel for returning the second effluent from said second ultrafilter to any one of the vessels containing respective glycosyltransferases is provided between said third selector valve and said vessels containing respective glycosyltransferase.

9. The sugar chain synthesizer according to claim 7, wherein any detector selected from the group consisting of a refractive index detector (RI), an ultraviolet-visible detector (UV), and a diode array detector (DAD) is provided between said GPC column and said first selector valve.

* * * * *